US007037515B2

(12) United States Patent
Kalafsky et al.

(10) Patent No.: US 7,037,515 B2
(45) Date of Patent: May 2, 2006

(54) ANHYDROUS INSECT REPELLENT COMPOSITION

(75) Inventors: Robert E. Kalafsky, Ogdensburg, NJ (US); Andrew H. Pechko, Ridgewood, NJ (US); Mark Garrison, Suffern, NY (US)

(73) Assignee: Avon Products Inc., New York, NY (US)

( * ) Notice: Subject to any disclaimer, the term of this patent is extended or adjusted under 35 U.S.C. 154(b) by 0 days.

(21) Appl. No.: 10/343,385

(22) PCT Filed: Nov. 26, 2001

(86) PCT No.: PCT/US01/44257

§ 371 (c)(1),
(2), (4) Date: Jun. 2, 2003

(87) PCT Pub. No.: WO02/43489

PCT Pub. Date: Jun. 6, 2002

(65) Prior Publication Data

US 2003/0191154 A1  Oct. 9, 2003

Related U.S. Application Data

(63) Continuation-in-part of application No. 09/470,474, filed on Dec. 22, 1999.

(51) Int. Cl.
*A01N 25/10* (2006.01)
(52) U.S. Cl. .................... 424/406; 424/43; 424/59; 424/60; 424/401; 424/403; 424/405; 424/407; 424/409; 424/420; 424/DIG. 10; 514/315; 514/551; 514/729; 514/919

(58) Field of Classification Search ................ 424/59, 424/60, 400, 401, 405–407, 43, 403, 409, 424/420, DIG. 10; 514/919, 551, 315, 729
See application file for complete search history.

(56) References Cited

U.S. PATENT DOCUMENTS

| 4,127,672 | A | * | 11/1978 | Klier et al. ................ 424/311 |
| 5,130,136 | A | | 7/1992 | Shono et al. |
| 5,227,406 | A | | 7/1993 | Beldock et al. |
| 5,346,922 | A | | 9/1994 | Beldock et al. |
| 5,621,013 | A | | 4/1997 | Beldock et al. |
| 5,648,398 | A | | 7/1997 | Beldock et al. |
| 5,672,337 | A | * | 9/1997 | Ascione et al. ............... 424/59 |
| 5,698,209 | A | | 12/1997 | Shono et al. |
| 5,882,633 | A | * | 3/1999 | Pisson et al. ................ 424/5.9 |

FOREIGN PATENT DOCUMENTS

| WO | WO 98/19537 | 5/1998 |
| WO | WO 98/19538 | 5/1998 |
| WO | 9827933 | * 7/1998 |

* cited by examiner

*Primary Examiner*—Neil S. Levy
(74) *Attorney, Agent, or Firm*—Ohlandt, Greeley, Ruggiero & Perle, L.L.P.

(57) ABSTRACT

There is provided a topical composition that comprises (a) a substantially anhydrous insect repellent selected from the group consisting of ethyl 3-(N-butylacetylamino) propionate or a derivative thereof, p-menthane-3,8-diol, hydroxyethyl isobutyl piperidine carboxylate (1-piperidine carboxylic acid), and mixtures thereof, and (b) a non-volatile solvent. A second embodiment of the present composition includes the same insect repellent, and a volatile solvent, and, optionally, a film former. A third embodiment includes the same insect repellent, a non-volatile solvent, a volatile solvent, and, optionally, a film former.

28 Claims, No Drawings

ANHYDROUS INSECT REPELLENT COMPOSITION

RELATED APPLICATIONS

This application is a national stage application having priority from PCT/US01/44257, filed Nov. 26, 2001, and U.S. Ser. No. 09/724,140, filed Nov. 28, 2000.

BACKGROUND OF THE INVENTION

1. Field Of The Invention

The present invention relates to insect repellent compositions. More particularly, the present invention relates to substantially anhydrous insect repellent compositions that are also water resistant/waterproof, as well as sweat resistant sweatproof. The composition may also provide ultraviolet (UV) sunscreen protection from both UVA and UVB radiation. As used herein, the term "insect" is intended to mean any insect or arachnid.

2. Description of the Prior Art

Humans have long sought protection against insects. Probing and blood engorgement from insects can be annoying, painful, and sometimes may result in allergic reactions. More importantly, insects may act as vectors of diseases, such as West Nile virus and Malaria, which can be transmitted to humans. Thus, it is particularly important to repel insects from humans to prevent annoying or painful insect bites, allergic reactions, as well as it may reduce the risk of disease.

Outdoor daytime activities that expose consumers to annoying insects also expose consumers to the damaging effects of UV exposure from the sun. Scientific literature has provided an abundance of documentation regarding the harm caused by extended, unprotected exposure to UV radiation. Consumers are also aware of the potential damage that results from extended, unprotected exposure to UV radiation. Thus, consumers prefer skin products that offer UV protection.

Consumers who expose themselves to both insects and UV radiation during outdoor activity often perspire or are, in some manner, exposed to water. As a result, it is important to provide an insect repellent composition that provides uniform coverage over the peaks and valleys of the skin surface, is water resistant and/or waterproof, sweat resistant and/or sweatproof, and rub resistant and/or proof, and has sunscreen activity.

Compositions with insect repellent properties have been developed to provide protection against insect bites. Some such compositions also have a sunscreen. These compositions are typically applied to the skin before an anticipated exposure.

In water-containing emulsions and similar aqueous product forms, the insect repellent active does not become effectively available on the skin until such time as the water in the composition evaporates off and the composition dries on the skin. The start of the availability time typically takes fifteen minutes or more.

Anhydrous insect repellent compositions containing oil of citronella as the insect repellant are known. For example, U.S. Pat. Nos. 5,227,406 and 5,346,922 to Beldock et al. provide insect repellents that contain terpineol, citronella (oil of citronella), rhodinol extra, and/or geraniol. Both of these patents provide that a sunscreen may be incorporated into the insect repellent compositions. U.S. Pat. No. 5,648,398 provides that a fragrance may be added to the insect repellent compositions disclosed in U.S. Pat. Nos. 5,227,406 and 5,346,922.

U.S. Pat. No. 5,621,013, also to Beldock et al., provides insect repellents that contain citronella (oil of citronella), geraniol, crystalline 3,8 P-menthanediol, and terpineol and/or rhodinol (extra).

U.S. Pat. Nos. 5,130,136 and 5,698,209 to Sumitomo provide the use of p-menthanediol as an insect repellent.

There are also products on the market that include ethyl 3-(N-butylacetylamino) propionate. However, such ethyl 3-(N-butylacetylamino) propionate products are typically emulsions and have large amounts of water. For example, one such product, Soltan Maximum UVA Protection SPF25 lotion, has been tested and found to have water in an amount 58.3 percentage by weight (wt %) of the composition. The second such product, Nivea Sonne Anti-Mucken F4 lotion, has been tested and found to have 74 wt % water.

International Publication WO 98/19537 to Kurz et al. provides a stable, aqueous insect repellent formulation containing ethyl 3-(N-butylacetylamino) propionate stabilized with a buffer at high pH and high water concentrations.

International Publication WO 98/19538, also to Kurz et al., provides a stable, aqueous insect repellent formulation containing ethyl 3-(N-butylacetylamino) propionate stabilized with ethanol.

The references cited above that are directed to compositions having ethyl 3-(N-butylacetylamino) propionate require relatively large amounts of water. However, ethyl 3-(N-butylacetylamino) propionate in the presence of water may cause the ester group to hydrolyze to the corresponding carboxylic acid. Therefore, it is highly desirable to provide a stable substantially anhydrous insect repellent composition having one or more of the following insect repellents: ethyl 3-(N-butylacetylamino) propionate, p-menthane-3,8-diol, hydroxyethyl isobutyl piperidine carboxylate (1-piperidine carboxylic acid), or combinations thereof. None of the art cited above discloses such a topical composition, let alone such a composition that also has ultraviolet (UV) sunscreen protection from both UVA and UVB radiation, is water resistant and/or waterproof, is sweat resistant and/or sweatproof, and is resistant to rubbing and/or rub proof.

SUMMARY OF THE INVENTION

It is an object of the present invention to provide a substantially anhydrous insect repellent composition that provides uniform coverage of the skin surface when applied.

It is another object of the present invention to provide such an insect repellent composition that has an average insect repellent protection time equal to or greater than two hours.

It is yet another object of the present invention to provide such an insect repellent composition that has UVA/UVB protection.

It is a further object of the present invention to provide an insect repellent composition that provides instantaneous availability of the insect repellent and a continuous, even film on the skin that is resistant to water, sweat and/or rubbing.

It is still a further object of the present invention to provide such an insect repellent composition that is a pleasant smelling, moisturizing, elegant, and non-greasy, alcohol-containing formulation.

It is still yet a further object of the present invention to provide such an insect repellent composition that may be topically applied as a spray, gel, liquid, stick, mousse, foam, or in a towelette.

It is also a further object of the present invention to provide a method of repelling insects from the skin.

These and other objects of the present invention will become apparent by a substantially anhydrous topical composition that has (a) an insect repellent selected from the group consisting of ethyl 3-(N-butylacetylamino) propionate or a derivative thereof, p-menthane-3,8-diol, hydroxyethyl isobutyl piperidine carboxylate (1-piperidine carboxylic acid), and mixtures thereof; and (b) a non-volatile solvent.

Another embodiment of the present invention has the insect repellent specified above, and a volatile solvent, rather than a non-volatile solvent. This composition may further include a film former.

A third embodiment of the present invention has the insect repellent specified above, and both a volatile and a non-volatile solvent. Again, this composition may further include a film former.

DETAILED DESCRIPTION OF THE INVENTION

All percentages set forth herein are percentages by weight of the total composition unless otherwise specified.

The present invention provides a substantially anhydrous composition that offers insect repellency and, preferably, sunscreen protection. The term "substantially anhydrous" means that the composition preferably contains less than 3 wt % water or, more preferably, less than 1 wt % water. Most preferably, a composition according to the present invention contains no water.

In a first embodiment of the present invention, the insect repellent or repellent active is combined with a non-volatile solvent to provide instantaneous availability of the insect repellent, as well as an immediate, continuous, even film on the skin to provide uniform coverage over the peaks and valleys of the skin surface. In a second embodiment of the present composition, there is provided the insect repellent, a volatile solvent, and, preferably, a film former. This aggregate composition also provides instantaneous availability of the insect repellent, as well as a continuous, even film that uniformly covers the skin. A possible third embodiment useful for achieving the benefits of the present invention is the combination of the first and second embodiments, namely the insect repellent, the non-volatile solvent, the volatile solvent, and, optionally, a film former.

An insect repellent active useful in compositions according to the present invention is ethyl 3-(N-butylacetylamino) propionate (also known as ethyl butylacetylamino propionate) or a derivative thereof, p-menthane-3,8-diol, hydroxyethyl isobutyl piperidine carboxylate (1-piperidine carboxylic acid), or any combination of these ingredients.

Ethyl 3-(N-butylacetylamino) propionate conforms to the formula:

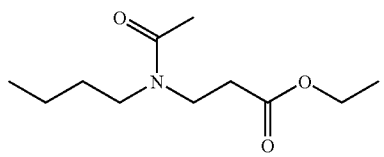

A preferred ethyl 3-(N-butylacetylamino) propionate is sold under the tradename IR 3535 by Merck Corporation.

The substantially anhydrous character of the present invention substantially enhances the stability of 3-(N-butylacetylamino) propionate because it significantly decreases the hydrolytic properties associated therewith, thereby providing greater efficacy and concentration of the insect repellent active in the film formed on the skin.

Another insect repellent useful in compositions according to the present invention is p-menthane-3,8-diol. This insect repellent conforms to the formula:

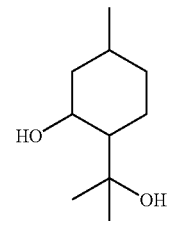

A preferred p-menthane-3,8-diol for use in the present invention is sold by Takasago International Corporation under the tradename Coolact 38D.

Yet another insect repellent useful in compositions according to the present invention is hydroxyethyl isobutyl piperidine carboxylate (1-piperidine carboxylic acid), which generally conforms to the following formula:

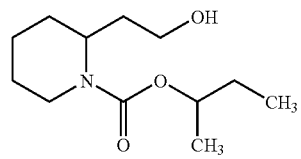

A preferred hydroxyethyl isobutyl piperidine carboxylate is sold by Bayer Corp. under the tradename KBR 3023.

The preferred insect repellent is ethyl 3-(N-butylacetylamino) propionate.

A composition conforming to any embodiment of the present invention has the insect repellent or repellent active in an amount about 0.1 wt % to about 85 wt % of the total weight of the composition. Preferably, the total amount of insect repellent is about 2.5 wt % to about 30 wt % or, more preferably, about 5 wt % to about 20 wt % based on the total weight of the composition.

A composition conforming to the first embodiment of the present invention includes a non-volatile solvent. The non-volatile solvents that can be used in the present invention include: vegetable oils; esters, such as octyl palmitate, $C_{12}$ to $C_{15}$ alkyl benzoates, isopropyl myristate and isopropyl palmitate; ethers, such as dicapryl ether and dimethyl isosorbide; fatty alcohols, such as cetyl alcohol, stearyl alcohol and behenyl alcohol; non-volatile silicones, such as dimethicone and polysiloxanes; hydrocarbon oils, such as mineral oil, petrolatum, isoeicosane and polyisobutene; polyols, such as propylene glycol, glycerin, butylene glycol, pentylene glycol and hexylene glycol; and waxes, such as beeswax and botanical waxes; and mixtures of the foregoing.

Any $C_{12}$ to $C_{15}$ alkyl benzoate non-volatile solvent known in the art may be used in the present invention. A preferred $C_{12}$ to $C_{15}$ alkyl benzoate is available from Finetex under the registered trademark Finsolve TN.

The amount of the non-volatile solvent in compositions conforming to the first embodiment of the present invention is preferably about 5 wt % to about 95 wt % based on the total weight of the composition. More preferably, the total amount of the non-volatile solvent is about 10 wt % to about 90 wt % or, most preferably, about 20 wt % to about 80 wt % based on the total weight of the composition.

A composition conforming to the second embodiment of the present invention has a volatile solvent. The volatile solvent basically improves the feel of the insect repellent composition against the skin.

The volatile solvents for use in the present composition include alcohols, such as ethanol and isopropanol; volatile silicones, such as cyclomethicone; and isoparaffins, such as iso-octane, isodedecane and isohexadecane.

The amount of volatile solvent in a compositions conforming to the second embodiment of the present invention is present in an amount about 5 wt % to about 85 wt %. More preferably, the volatile solvent is present in an amount about 5 wt % to about 65 wt % or, most preferably, about 5 wt % to about 55 wt % based on the total weight of the composition.

In both the first and the second embodiments of the present invention, the composition may include a film former. The film former is preferably a waterproofing film former that serves to provide resistance to water, sweat and/or rubbing. In other words, a waterproofing film former enables the composition to be waterproof, sweatproof, and/or rub proof. When used, a waterproofing film former may preferably be present in an amount up to about 20 wt % or, more preferably, up to about 10 wt % or, most preferably, up to about 5 wt %, based on the total weight of composition. The waterproofing film former is especially useful in composition conforming to the second embodiment of the present invention.

The following Table 1 lists film formers that can be used in the present compositions along with preferred and more preferred ranges of each.

TABLE 1

| Waterproofing Film Formers | Preferred Range wt % | More Preferred Range wt % |
| --- | --- | --- |
| C-15 alkyl galactomannan | 0.10–5.00 | 0.10–2.00 |
| Isododecane/ethylene mixed copolymer | 3.0–20.0 | 5.0–15.0 |
| Adipic acid/diethylene glycol/glycerin crosspolymer | 1.0–10.0 | 1.0–5.0 |
| Trimethylpentanediol/adipic acid copolymer | 1.0–10.0 | 1.0–5.0 |
| Trimethylpentanediol/adipic acid/isononanoic acid | 1.0–10.0 | 1.0–5.0 |
| Polyvinylpyrrolidone (PVP)/hexadecene copolymer (e.g., GANEX V-216) | 0.5–10.0 | 1.0–5.0 |
| Polyvinylpyrrolidone (PVP)/eicosene copolymer (e.g. GANEX V-220) | 0.5–10.0 | 1.0–5.0 |
| *Tricontonyl PVP | 0.5–10.0 | 1.0–5.0 |
| *Alpha olefin/isopropyl maleate/MA polymer | 1.0–10.0 | 1.0–5.0 |
| Cycloalkyl methacrylate copolymer/isododecane | 1.0–15.0 | 2.0–12.0 |
| Trimethyl polysiloxane | 1.0–10.0 | 1.0–5.0 |
| Octadecene/MA copolymer | 0.5–10.0 | 1.0–5.0 |
| Polypropylene glycol 12 (PPG-12)/saturated methylene diphentldiisocynanate (SMDI) | 1.0–10.0 | 1.0–5.0 |
| Acrylates C10–30 alkyl acrylate crosspolymer | 0.10–5.0 | 0.10–2.0 |
| Cetyl hydroxyethylcellulose | 0.10–5.0 | 0.10–2.0 |
| *Dimethiconol | 1.0–20.0 | 1.0–10.0 |
| *Dimethicone | 1.0–20.0 | 1.0–10.0 |
| *Diglycol/cyclohexane dimethanol/isophthalates/sulfoisophthalate copolymer | 1.0–10.0 | 1.0–5.0 |
| Acrylates Octylacrylamide Copolymer | 1.0–10.0 | 1.0–5.0 |
| *Polyurethane | 1.0–20.0 | 1.0–10.0 |
| Polyethylene | 0.10–10 | 1.0–5.0 |
| Beeswax | 0.5–5.0 | 1.0–5.0 |

The asterisk denotes the more preferred film formers.

A composition conforming to the third embodiment of the present invention has an insect repellent together with a non-volatile solvent (as described in reference to the first embodiment), volatile solvent (as described in reference to the second embodiment), and, optionally, a film former. It has been found that, like the first and second embodiments, the third embodiment of the present invention provides for instantaneous availability of the insect repellent active and a continuous and even film that uniformly covers the peaks and valleys of the skin surface.

The amount of the volatile solvent in a composition conforming to the third embodiment can be about 3 wt % to about 55 wt % based on the total weight of the composition or, preferably, about 3 wt % to about 45 wt %. The amount of the non-volatile solvent in a composition according to the third embodiment can be about 2 wt % to about 40 wt % or, more preferably, about 2 wt % to about 30 wt %, based on the total weight of the composition.

A composition conforming to the third embodiment of the present invention can include a film former. Several film formers useful in a composition conforming to the third embodiment of the present invention, and the relative percentage weights thereof, have been set forth above.

A preferred vehicle for an insect repellent composition according to the present invention contains alcohol. A preferred vehicle contains about 5 wt % to about 40 wt % of any suitable cosmetic grade alcohol. Preferably, the cosmetic grade alcohol is a denatured alcohol. The preferred alcohol is SD alcohol 40B.

A composition according to the present invention preferably includes one or more sunscreens known in the art for providing UVA and/or UVB protection. Preferably, sunscreens for use in compositions according to the present invention can used with a topical alcohol-containing vehicle.

Among the sunscreens that may be used in an insect repellent composition according to the present invention are sunscreens from the following categories (or their derivatives): para-aminobenzoic acid ("paba"), benzophenone, cinnamic acid, cinnamate esters, camphor, anthranilic acids, salicylates, benzotriazole, oxazoles, urocanic acids, dibenzoyl methanes, benzoic acid, diphenyl acrylates, gallic acids, titanium dioxides, zinc oxides and sunscreens having a propane 1,3-dione moiety, and combinations thereof.

More specific examples of sunscreens useful in the present invention include: octyl methoxy cinnamate, octyl salicylate, octocrylene, butyl methoxydibenzoylmethane, oxybenzone, dioxybenzone, menthyl anthranilate, para aminobenzoic acid (PABA), DEA methoxycinnamate, homomenthyl salicylate, octyl dimethyl PABA, TEA salicylate, titanium dioxide, zinc oxide, 4-methyl benzilidene camphor, octyl triazone, ethyl PABA, 2-(2'-hydroxy-5'-methylphenyl) benzotriazole, terephthalydiene dicamphorsulfonic acid, methylene bis-benzotriazolyl tetramethylbutylphenol, phenylbenzimidazole sulfonic acid, bis-ethylhexyloxyphenol methoxyphenol triazine, and salts, and mixtures thereof.

Examples of preferred sunscreens, and the preferred amounts, are:

| Sunscreen | Percentage (wt %) |
| --- | --- |
| oxybenzone | 2 to 10 |
| dioxybenzone | 1 to 3 |
| menthyl anthranilate | 3 to 6 |
| para aminobenzoic acid (PABA) | 5 to 15 |
| DEA methoxycinnamate | 8 to 10 |
| octocrylene | 2 to 15 |
| octyl methoxycinnamate | 2 to 10 |
| octyl salicylate | 3 to 10 |
| homomenthyl salicylate | 4 to 15 |
| octyl dimethyl PABA | 1.4 to 5 |
| TEA salicylate | 5 to 12 |
| titanium dioxide | 2 to 25 |
| zinc oxide | 2 to 25 |
| butylmethoxy dibenzoylmethane (avobenzone)** | 0.1 to 5 |
| 4-methyl benzilidene camphor | 0.1 to 6 |
| octyl triazone | 0.1 to 10 |
| ethyl PABA | 1 to 10 |
| 2-(2'hydroxy-5'-methylphenyl)benzotriazole*** | 0.5 to 10 |
| methylene bis-benzotriazolyl tetramethylbutylphenol***** | 1 to 10 |
| bis-ethylhexyloxyphenol methoxyphenol triazine***** | 1 to 10 |
| terephthalydiene dicamphor sulfonic acid | 0.1 to 20 |

**A non-limiting example of butylmethoxy dibenzoylmethane is available from Givaudan under the tradename "PARSOL 1789".
***A non-limiting example of 2-(2'hydroxy-5'-methylphenyl) benzotriazole is available from Ciba-Geigy under the tradename "TINUVIN P".
*****A non-limiting example of methylene bis-benzotriazolyltetramethylbutylphenol is available from Ciba-Geigy under the tradename "TINOSORB-M".
*****A non-limiting example of bis-ethylhexyloxyphenol methoxyphenol triazine is available from Ciba-Geigy under the tradename "TINOSORB-S".

More preferred sunscreens include: methyl benzylidene camphor, octyl methoxycinnamate, 4-(1,1-dimethylethyl)4'-methoxy dibenzoylmethane (PARSOL 1789), benzophenone-3, octocrylene, and octyl salicylate, titanium dioxide, and combinations thereof.

The amount of sunscreen in the compositions is about 0.1 wt % to about 40 wt % based on the total weight of the composition.

Preferably, the composition of the present invention has about 5 wt % to about 10 wt % octyl methoxy cinnamate, up to about 10 wt % octyl salicylate, up to about 15 wt % octocrylene, and up to 5 wt % butyl methoxydibenzoylmethane, based on the total weight of the composition. Most preferably, the composition has about 7.5 wt % octyl methoxycinnamate, about 5 wt % octyl salicylate, about 10 wt % octocrylene, and about 3 wt % butyl methoxydibenzoylmethane, based on the total weight of the composition.

A composition according to the present invention may include other ingredients. For example, an emollient may be used that has good spreadability, chemical stability, and miscibility with alcohol. Any emollient that exhibits the above-identified characteristics may be used to practice this invention.

When used, an emollient is preferably present in an amount about 20 wt % to about 40 wt % based on the total weight of the composition.

The compositions of the present invention may also contain an antioxidant, which is preferably incorporated in the vehicle. The preferred antioxidant is butylated hydroxytoluene. The antioxidant is present from about 0.01 wt % to about 0.1 wt % based on the total weight of the composition.

The compositions of the present invention may also contain a fragrance that will provide a pleasant smell to the present invention, but will not adversely affect the effectiveness of the insect repellent composition. Like the antioxidant, the fragrance is preferably part of the vehicle. A fragrance can be present in an amount about 0.1 wt % to about 5.0 wt % based on the total weight of the composition. More preferably, a fragrance is present in an amount about 0.5 wt % based on the total weight of the insect repellent composition.

A composition according to the present invention may also include a viscosity modifier and/or thickener, such as hydroxypropyl cellulose, to aid in making the composition, for example, a gel or an aerosol dispensable product.

The compositions of the present invention may also contain a secondary insect repellent, such as oil of citronella, soy bean oil, lemon grass oil, geranium/geraniol oil, and mixtures thereof, and may be added preferably in the vehicle.

The following are examples of preferred compositions according to the present invention:

| Component | approximate wt % |
| --- | --- |
| Example 1 | |
| isononyl isonanoate | 29.9 |
| $C_{12-15}$ alkyl benzoate | 20 |
| isopropyl myristate | 20 |
| ethyl butylacetylaminoproprionate | 15 |
| octyl palmitate | 10 |
| canola oil | 5 |
| tocopheryl acetate | 0.1 |
| Example 2 | |
| butylene glycol | 49.9 |
| $C_{12-15}$ alkyl benzoate | 25 |
| isononyl isonanoate | 15 |
| p-methane-3,8-diol | 10 |
| oil of citronella | 0.1 |
| Example 3 | |
| isononyl isonanoate | 41.5 |
| ethyl butylacetylaminoproprionate | 20 |
| Avobenzone | 10 |
| hexylene glycol | 10 |
| octyl methoxycinnamate | 7.5 |
| Oxybenzone | 6 |
| octyl salicylate | 5 |
| Example 4 | |
| Cyclomethicone | 38 |
| ethanol | 30 |
| N,N diethyltoluamide | 20 |
| isohexadecane | 10 |
| acrylates/octylacrylamide copolymer | 2 |
| Example 5 | |
| Ethanol | 50 |
| soybean oil | 20 |
| DEET | 20 |
| Isododecane | 10 |

-continued

| Component | approximate wt % |
|---|---|
| Example 6 | |
| Ethanol | 50 |
| lemon grass oil | 20 |
| oil of citronella | 10 |
| p-menthane-3,8-diol | 10 |
| Geraniol | 5 |
| PPG-12/SMDI copolymer | 5 |
| Example 7 | |
| Ethanol | 37.5 |
| ethyl buytlacetylaminoproprionate | 15 |
| propylene glycol dipelargonate | 10 |
| N,N diethyltoluamide | 10 |
| 1-piperidine carboxylic acid | 10 |
| octyl methoxycinnamate | 7.5 |
| Octocrylene | 7 |
| acrylates/octylacrylamide copolymer | 3 |
| Example 8 | |
| Ethanol | 27 |
| p-methane-3,8-diol | 20 |
| lemon grass oil | 20 |
| oil of citronella | 10 |
| isononyl isonanoate | 8 |
| PPG-12/SMDI copolymer | 5 |
| soybean oil | 5 |
| Geraniol | 5 |

Each of the above embodiments of the insect repellent composition may be applied directly to the consumer's skin. It is believed that the insect repellent composition will provide an average insect repellent protection time equal to or greater than 2 hours.

The present invention also includes a method of repelling insects from the skin. The method includes topically applying an effective amount of any of the insect repellent compositions of the present invention to the skin.

A composition according to the present invention may be applied to a consumer's skin as a spray product (either pump or aerosol), liquid, stick, gel, mousse, or foam. Alternatively, any of the compositions may be incorporated into a towelette that may use to topically apply the insect repellent composition by rubbing the towelette against skin.

Accordingly, the present invention provides a composition that (1) contains the claimed insect repellent actives, (2) is substantially anhydrous, (3) provides instantaneous availability of the insect repellant active when applied to the skin, (4) provides a continuous and even film on the skin surface for maximum uniform coverage over the peaks and valleys of the skin, and (5) is stable. Applicants respectfully submit that nothing in the prior art teaches or suggests the present invention.

The present invention is not limited to the examples illustrated above, as it is understood that one ordinarily skilled in the art would be able to utilize substitutes and equivalents without departing from the present invention.

We claim:

1. An insect repellent composition comprising:
    an insect repellent selected from the group consisting of ethyl 3-(N-butylacetylamino) propionate, p-menthane-3,8-diol, hydroxyethyl isobutyl piperidine carboxylate, and any combinations thereof;
    a cosmetically acceptable vehicle having a non-volatile solvent selected from the group consisting of one or more esters, ethers, vegetable oils, fatty alcohols, non-volatile silicones, polyols, waxes, and any combinations thereof; and
    a film former selected from the group consisting of acrylates octylacrylamide copolymer, polyurethane, and a combination thereof,
    wherein the composition is substantially anhydrous.

2. The insect repellent composition of claim 1, wherein said insect repellent is present in an amount about 0.1 wt % to about 85 wt % based on the total weight of the composition.

3. The insect repellent composition of claim 1, wherein said insect repellent is present in an amount about 2.5 wt % to about 30 wt % based on the total weight.

4. The insect repellent composition of claim 1, wherein said non-volatile solvent is selected form the group of C12 to C15 alkyl benzoate.

5. The insect repellent composition of claim 1, wherein the non-volatile solvent comprises about 5 wt % to about 95 wt % based on the total weight of the composition.

6. The insect repellent composition of claim 1, wherein the nonvolatile solvent comprises about 20 wt % to about 80 wt % based on the total weight of the composition.

7. The insect repellent composition of claim 1, further comprising a volatile solvent.

8. The insect repellent composition of claim 7, wherein said non-volatile solvent comprises about 2 wt % to about 40 wt %, and said volatile solvent comprises about 3 wt % to about 55 wt %, based on the total weight to the composition.

9. The insect repellent composition of claim 1, wherein the film former is acrylates octylacrylamide copolymer.

10. The insect repellent composition of claim 1, wherein the film former is acrylates octylacrylamide copolymer.

11. The insect repellent composition of claim 1, wherein the insect repellent is ethyl 3-(N-butylacetylamino) propionate.

12. The insect repellent composition of claim 1, further comprising an additional film former selected from the group consisting of one or more of C-15 alkyl galactomannan, isododecane/ethylene mixed copolymer, adipic acid/diethyl glycol/glycerin cross polymer, trimethylpentanediol/adipic acid copolymer, trimethylpentanediol/adipic acid/isononanoic acid, polyvinylpyrrolidone (PVP) /hexadecene copolymer, PVP/eicosene copolymer, tricontonyl PVP, alpha olefin/isopropyl maleate/methyl acrylate (MA) polymer, cycloalkyl methacrylate copolymer/isododecane, trimethyl polysiloxane, octadecene/MA copolymer, polypropylene glycol 12 (PPG-12)/SMDI copolymer, diglycol/cyclohexane/dimethanol/isophthalate/sulfoisophthalate copolymer, polyethylene, and any combinations thereof.

13. The insect repellent composition of claim 1, wherein the composition is in the form selected from the group consisting of a stick, a spray, a liquid, a gel, a mousse, a foam, and a towelette.

14. The insect repellent composition of claim 1, wherein the composition provides an average insect repellent protection time of equal to or greater than 2 hours.

15. A method of repelling insects from a skin comprising applying to the skin the insect repellent composition of claim 1 in an amount effective for repelling insects.

16. The method of claim 15, wherein said insect repellent composition has an insect repellent active in an amount about 2.5 wt % to about 30 wt % based on the total weight of the composition.

17. An insect repellent composition 1, comprising:
    an insect repellent selected from the group consisting of ethyl 3-(N-butylacetylamino) propionate, p-menthane- 3,8-diol, hydroxyethyl isobutyl piperidine carboxylate, and any combinations thereof;
a film former selected from the group consisting of acrylates octylacrylamide copolymer, polyurethane, and a combination thereof;
a cosmetically acceptable vehicle having a volatile solvent,
wherein the composition is substantially anhydrous.

18. The insect repellent composition of claim 17, wherein said insect repellent comprises about 0.1 wt % to about 85 wt % based on the total weight of the composition.

19. The insect repellent composition of claim 17, wherein said insect repellent is present in an amount about 2.5 wt % to about 30 wt % based on the total weight of the composition.

20. The insect repellent composition of claim 17, wherein said volatile solvent is selected from the group consisting of one or more alcohols, silicones, isoparaffins, and any combinations thereof.

21. The insect repellent composition of claim 17, wherein said volatile solvent is present in an amount about 5 wt % to about 85 wt % based on the total weight of the composition.

22. The insect repellent composition of claim 17, wherein said volatile solvent comprises 5 wt % to about 55 wt % based on the total weight of the composition.

23. The insect repellent composition of claim 17, further comprising an additional film former selected from the group consisting of one or more of C-15 alkyl galactomannan, isododecane/ethylene mixed copolymer, adipic acid/ diethyl glycol/glycerin cross polymer, trimethylpentanediol/ adipic acid copolymer, trimethylpentanediol/adipic acid/ isononanoic acid, polyvinylpyrrolidone (PVP)/hexadecene copolymer, PVP/eicosene copolymer, tricontonyl PVP, alpha olefin/isopropyl maleate/methyl acrylate (MA) polymer, cycloalkyl methacrylate copolymer/isociodecane, trimethyl polysiloxane, octadecene/MA copolymer, polypropylene glycol 12 (PPG-12)/SMDT copolymer, diglycol/ cyclohexane/dimethanol/isophthalate/sulfoisophthalate copolymer, polyethylene, and any combinations thereof.

24. The insect repellent composition of claim 17, wherein the film former is acrylates octylacrylamide copolymer.

25. The insect repellent composition of claim 17, wherein the insect repellent is ethyl 3-(N-butylacetylamino) propionate.

26. A method of repelling insects from skin comprising the step of applying the insect repellent composition of claim 17 to the skin in an amount effective to repel insects.

27. The insect repellent composition of claim 1, wherein the insect repellent is ethyl 3-(N-butylacetylamino) propionate, wherein the non-volatile solvent is C12–15 alcohols benzoate, and wherein the film former is acrylates octylacrylamide copolymer.

28. The insect repellent composition of claim 17, wherein the insect repellent is ethyl 3-(N-butylacetylamino) propionate, wherein the volatile solvent is ethanol, and wherein the film former is acrylates octylacrylamide copolymer.

* * * * *